United States Patent [19]

Darr et al.

[11] Patent Number: 5,538,010

[45] Date of Patent: Jul. 23, 1996

[54] BIOPSY NEEDLE DEVICE

[75] Inventors: Allan Darr, State College, Pa.; Dan C. Ireland, Martinsville, Ind.

[73] Assignee: Proact Ltd., State College, Pa.

[21] Appl. No.: 318,216

[22] Filed: Oct. 5, 1994

[51] Int. Cl.⁶ ..................................................... A61B 10/00
[52] U.S. Cl. ......................................................... 128/754
[58] Field of Search .................................... 128/751–754; 606/167, 170

[56] References Cited

U.S. PATENT DOCUMENTS

| Re. 34,056 | 9/1992 | Lindgren et al. | 128/754 |
|---|---|---|---|
| 3,989,033 | 11/1976 | Halpern et al. | 128/2 B |
| 4,308,875 | 1/1982 | Young | 128/753 |
| 4,600,014 | 7/1986 | Beraha | 128/754 |
| 4,699,154 | 10/1987 | Lindgren | 128/754 |
| 4,702,261 | 10/1987 | Cornell et al. | 128/754 |
| 4,735,215 | 4/1988 | Goto et al. | 128/754 |
| 4,766,907 | 8/1988 | de Groot et al. | 128/754 |
| 4,776,346 | 10/1988 | Beraha et al. | 128/754 |
| 4,944,308 | 7/1990 | Akerfeldt | 128/751 |
| 4,953,558 | 9/1990 | Akerfeldt | 128/751 |
| 4,958,625 | 9/1990 | Bates et al. | 128/754 |
| 5,121,751 | 6/1992 | Panalletta | 128/754 |
| 5,163,947 | 11/1992 | Kvalo et al. | 606/151 |

FOREIGN PATENT DOCUMENTS

| WO83/00112 | 1/1983 | WIPO . |
|---|---|---|
| WO83/03343 | 10/1983 | WIPO . |

*Primary Examiner*—Max Hindenburg
*Attorney, Agent, or Firm*—Woodard, Emhardt, Naughton, Moriarty & McNett

[57] ABSTRACT

A biopsy needle device includes a needle assembly (30) sequentially driven by a spring loaded drive mechanism (44). The needle assembly (30) includes an outer cannula (12) through which a stylet (14) is slidably projected to cut and capture a core of the diagnostic tissue. The cannula (12) and stylet (14) slide on a pair of longitudinal rails (34, 36). A drive carriage (60) follows the path of a pair of cam guide grooves (56, 58), such that the carriage sequentially engages and displaces the cannula (12) and stylet (14), thereby producing the requisite sequential motion of the cannula (12) and stylet (14).

19 Claims, 6 Drawing Sheets

BIOPSY NEEDLE DEVICE

TECHNICAL FIELD OF THE INVENTION

The present invention relates to the performance of biopsies on living tissue, animal or human, and more particularly to an improved surgical instrument for performing such biopsy procedures.

BACKGROUND OF THE INVENTION

As used herein, the term "biopsy" refers to the collection of a soft tissue specimen for purposes of examination, disease identification and diagnosis. Typically, biopsy procedures are performed to obtain specimens of tissue from an internal organ of suspect for detection of disease conditions, such as cancer, and are of particular utility in determining the extent of the spread of the disease prior to the performance of surgery or therapy. Where, for instance, an abnormality is suspected in a deeply located soft tissue organ such as the liver, spleen, pancreas, glands, etc., or where a growth has been located and it is desired to determine the nature and extent of the growth, a biopsy may be performed in order to obtain tissue specimens for laboratory examination. In general, biopsy procedures are preferred over the difficulty and trauma of exploratory surgery.

Referring now to FIG. 1A, a two piece biopsy needle 10 is commonly employed for obtaining tissue core specimens and comprises a small diameter, long tubular cannula 12 and a long, thin, sharp-tipped stylet 14 located inside the cannula 12 and movable relative to the cannula. The stylet 14 is provided with a specimen notch 16 on its periphery near a proximal tip of the stylet. The promixal end of the cannula 12 may be sharpened.

The biopsy needle 10 is inserted through a small incision or puncture made in the skin and driven into the body until its sharpened end enters the organ 18 of suspect. During this insertion stage of the procedure, the stylet 14 is positioned within the cannula 12 so that no more than the sharp tip of the stylet 14 is exposed; the specimen notch 16 is covered by the cannula 12.

Referring now to FIG. 1B, once the instrument 10 has been positioned at the site for the biopsy, the stylet 14 is driven into the organ 18 far enough to expose the specimen notch 16 of stylet 14. Soft body tissues of the organ 18 will then prolapse into the specimen notch 16.

Referring now to FIG. 1C, the cannula 12 is then advanced along the stylet 14 in order to cover the specimen notch 16. This forward movement of the cannula 12 cuts out a specimen 20 of the prolapsed tissue, which specimen 20 becomes retained in the specimen notch 16 of the stylet 14. With the cannula 12 still concealing the specimen 20 in the specimen notch 16, the biopsy needle assembly 10 may then be withdrawn carefully from the target site. Thereafter, the cannula 12 is once again retracted in order to expose the specimen notch 16 of the stylet 14, creating access to the tissue specimen 20 contained therein.

In all biopsies, it is desirable to perform the cutting procedure quickly in order to prevent the prolapsed tissue in the specimen notch 16 from being displaced outwardly during advance of the cannula 12 along the stylet 14. Slow movement by the cannula 12 might result in an insufficient specimen 20 being obtained. Numerous prior art devices have been developed in order to automate the sequential advance of the stylet 14 and the cannula 12. In order the achieve the requisite precise and coordinated mechanical motions, the prior art devices utilize relatively complex mechanical systems requiring a large number of parts and complex assemblies. Because of this, such prior art devices tend to be relatively expensive, cumbersome and unreliable. There is therefore a need in the prior art for a biopsy needle device which incorporates a simplified design requiring fewer parts and therefore less complicated, more compact assembly. The present invention is directed toward meeting those needs.

SUMMARY OF THE INVENTION

An automatic biopsy needle device is disclosed. The biopsy needle device includes a cannula and stylet needle assembly sequentially driven by a spring loaded drive mechanism. The needle assembly includes an outer cannula through which a stylet is slidably projected to cut and capture a core of the diagnostic tissue. The cannula and stylet slide on a pair of longitudinal rails. A drive carriage follows the path of a pair of cam guide grooves, such that the carriage sequentially engages and displaces the cannula and stylet, thereby producing the requisite sequential motion of the cannula and stylet.

In one form of the invention, a biopsy needle device is disclosed, comprising a cannula, a stylet, a cannula slide member coupled to the cannula and operative to slide along a longitudinal axis in a first direction; a stylet slide member coupled to the stylet and operative to slide along the longitudinal axis in the first direction such that the stylet is carried partially within the cannula; a carriage, drive means for translating the carriage in a first direction, a cam guide pin coupled to the carriage, and a cam guide groove engaging the cam guide pin and operative to reciprocate the carriage in a second direction substantially perpendicular to the first direction while the carriage is translating in the first direction, wherein the carriage engages the stylet slide member, translates the stylet slide member in the first direction, disengages the stylet slide member and engages the cannula slide member when the carriage reciprocates in the second direction, and translates the cannula slide member in the first direction. In another form of the invention, a biopsy needle device is disclosed, comprising a cannula, a cannula slide member coupled to the cannula and operative to slide in a first direction; a stylet and a stylet slide member coupled to the stylet and operative to slide in the first direction such that the stylet is carried partially within the cannula; a carriage operative to reciprocate in a second direction while translating in the first direction, the second direction being substantially perpendicular to the first direction, wherein the carriage engages the stylet slide member, translates the stylet slide member in the first direction, disengages the stylet slide member and engages the cannula slide member when the carriage reciprocates in the second direction, and translates the cannula slide member in the first direction.

In another form of the invention, a method for performing a tissue biopsy is disclosed, comprising the steps of (a) engaging a carriage with a stylet, (b) translating the carriage and the stylet in a first direction, (c) reciprocating the carriage in a second direction while translating in the first direction, the second direction being substantially perpendicular to the first direction, (d) disengaging the carriage from the stylet, (e) engaging the carriage with a cannula, and (f) translating the carriage and the cannula in the first direction.

DESCRIPTION OF THE PREFERRED EMBODIMENT

For the purposes of promoting an understanding of the principles of the invention, reference will now be made to the preferred embodiments thereof, and specific language will be used to describe the same. It will nevertheless be understood that no limitation of the scope of the invention is thereby intended, such alterations, modifications, and further applications of the principles of the invention being contemplated as would normally occur to one skilled in the art to which the invention relates.

Figure 2:
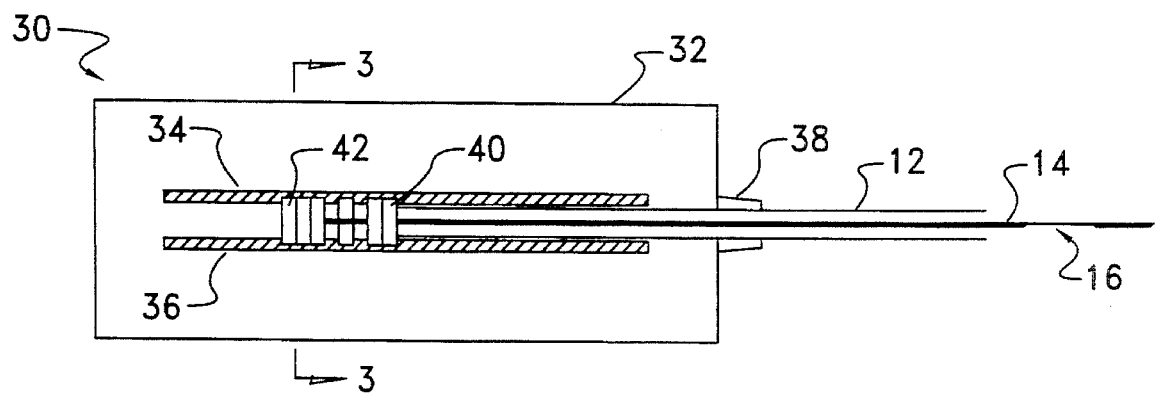
FIG. 2 is a plan view of an upper housing of a biopsy needle device of a first embodiment of the present invention.

The present invention is directed towards an improved biopsy needle device having a minimum number of components which may be assembled in a straightforward manner, thereby achieving a cost-effective, compact and reliable product. Referring now to FIG. 2, there is illustrated an upper housing of the biopsy needle device of a first embodiment of the present invention, indicated generally at 30. The upper housing 30 includes a support member 32 on which is carried a pair of rails 34 and 36. A cannula 12 projects through a guide tube 38 in the housing 32, and is secured to the rails 34 and 36 by a cannula slide member 40. The stylet 14 is slidingly carried within the cannula 12 and secured to the rails 34 and 36 by a stylet slide member 42. Cannula slide member 40 and stylet slide member 42 translate longitudinally on the rails 34 and 36, but are releasably held in the position shown by two detents (see FIG. 7). Various longitudinal translations of the cannula 12 and stylet 14 are possible by relative movement of the slide members 40 and 42.

Figure 3:
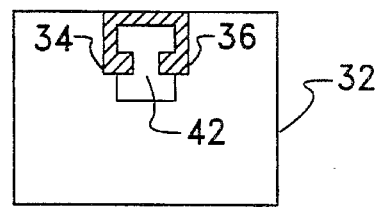
FIG. 3 is a cross-sectional view of the device of FIG. 2.

Referring now to FIG. 3, the upper housing 30 of FIG. 2 is shown in cross-section. It will be appreciated by those skilled in the art that the slide member 42 (as well as the slide member 40) is free to translate longitudinally along the rails 34 and 36. The interlocking design of the rails 34 and 36 relative to the slide members 40 and 42 remove any possibility of the slide members 40 and 42 becoming disengaged from the rails 34 and 36 during longitudinal travel thereon.

Figure 4:
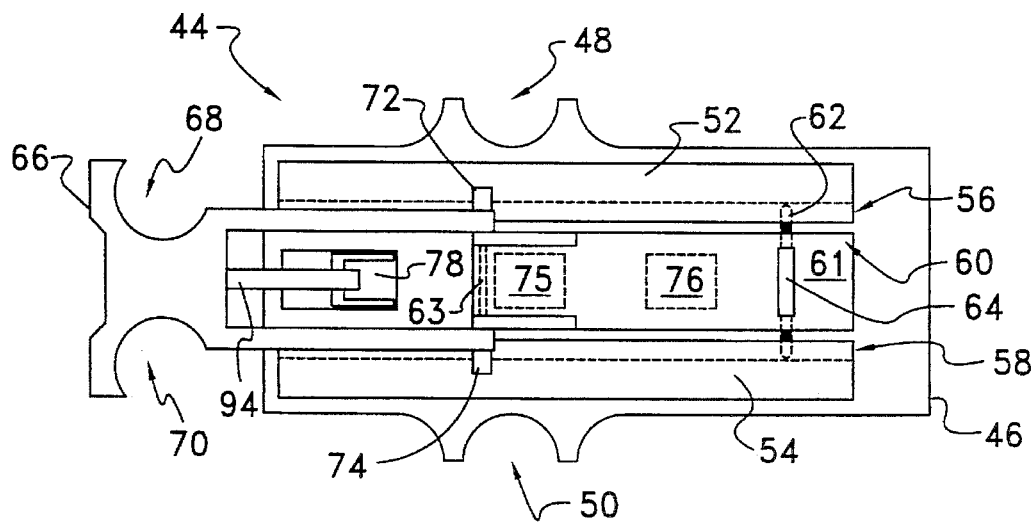
FIG. 4 is a plan view of a lower housing of the biopsy needle device of a first embodiment of the present invention.

Referring now to FIG. 4, there is illustrated a lower housing portion of the biopsy needle device of the first embodiment of the present invention, indicated generally at 44. Lower portion 44 includes a base member 46 having finger hold means 48 and 50. A first guide member 52 and second guide member 54 are coupled to the base 46 in order to form cam guide grooves 56 and 58, respectively, along their interior edges. Cam guide grooves 56 and 58 have a non-linear longitudinal shape, as shown schematically in FIG. 7. Positioned between first and second guide members 52 and 54 is a carriage 60 which is coupled to the cam guide grooves 56 and 58 via transverse cam follower pins 62 and 63. Affixed to the carriage 60 and overlying the cam follower pin 62 is a slide engagement member 64. A handle 66, including finger grips 68 and 70, has bifurcated end portions which engage a pair of elevated carriage engagement tabs 72 and 74. The carriage 60 includes a plate 61, the underside of which includes recesses 75 and 76 for engagement with a flexible detent 78 when the carriage 60 is retracted longitudinally along the cam guide grooves 56 and 58. The flexible detent 78 is mounted to the base 46. The two recesses 75 and 76 allow the carriage to be cocked at two different positions. In the first position, recess 75 is engaged with detent 78, whereby cannula slide member 40 is retracted, exposing the specimen notch 16 (see FIG. 7C). This allows access to the specimen 20 after the biopsy is complete. In the second position, recess 76 is engaged with detent 78, whereby the device is fully cocked and ready for sampling (see FIG. 7A).

It will be appreciated by those skilled in the art that the carriage 60 is forced to follow the path of the cam guide grooves 56 and 58 during longitudinal translation because of its engagement therewith through cam follower pins 62 and 63. It is therefore possible to impart a variety of sequential motions to the carriage 60 by design of the cam guide grooves 56 and 58.

Figure 5:
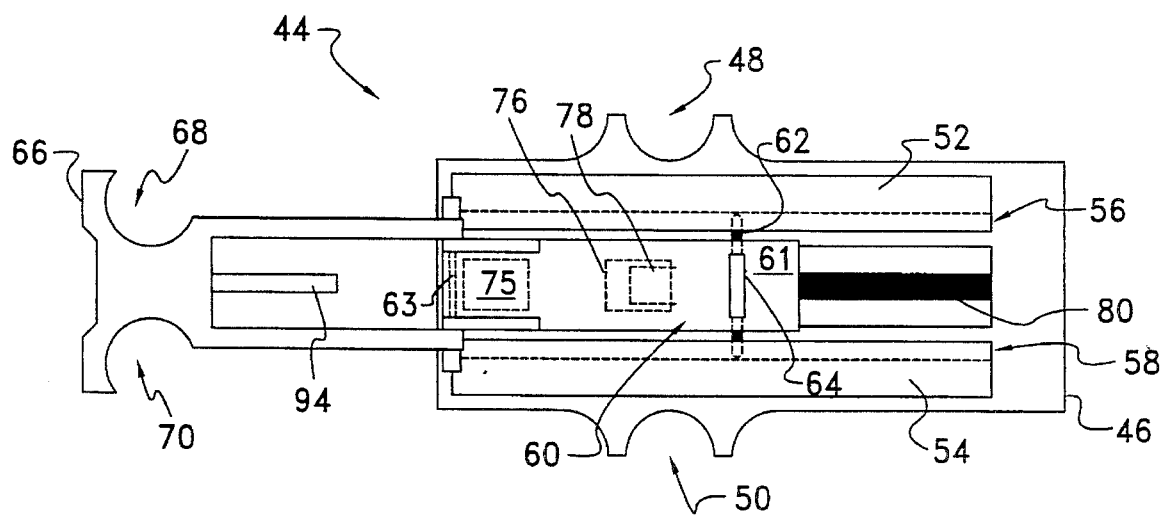
FIG. 5 is a plan view of the device of FIG. 4, shown in a retracted and cocked position.
Figure 6:
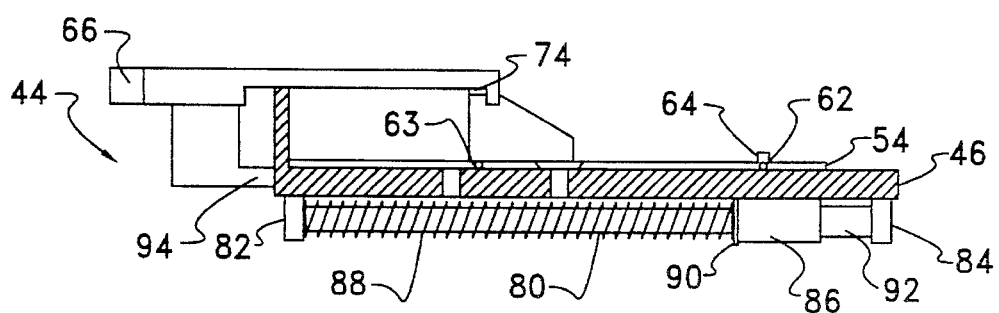
FIG. 6 is a side plan view of the device of FIG. 4.

Referring now to FIG. 5, the second portion 44 is illustrated with the carriage 60 retracted fully to the left, with the detent 78 engaged with the recess 76, thereby retaining the carriage 60 in the position illustrated. Visible in the illustration of FIG. 5 is a spring guide rod 80 which is attached to the underside of base 46 (as more clearly illustrated in FIG. 6). The spring guide rod 80 is coupled to the base 46 via rod mounting portions 82 and 84. The carriage 60 is coupled to the spring guide rod 80 via a recess cylindrical mounting member 86 extending from carriage plate 61. A helical drive spring 88 is concentrically mounted on spring guide rod 80 and abuts the rod mounting member 82 and a washer 90. When the carriage 60 is retracted to the left by pulling handle 66, the helical drive spring 80 is compressed, thereby storing a driving force which is opposed by the detent 78 engagement with the recess portion 76. The range of motion of the carriage 60 to the right is limited by a spacer 92 concentrically mounted on spring guide rod 80.

Figure 1A:
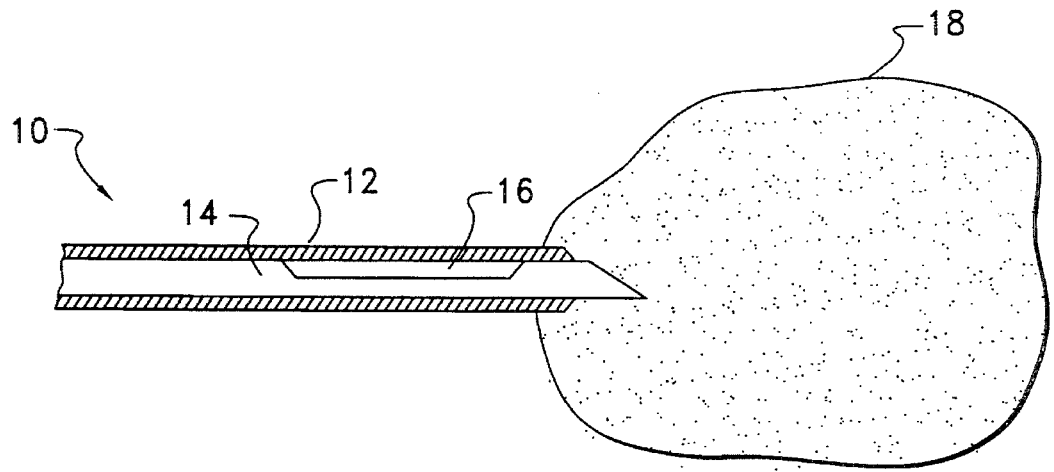
FIGS. 1A–C are cross-sectional views illustrating a prior art tissue biopsy needle assembly and method.
Figure 1B:
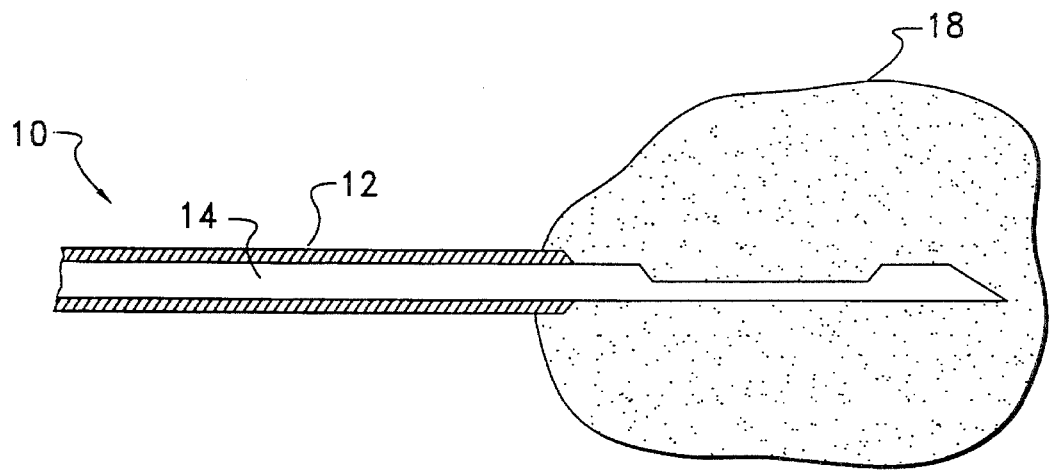
Figure 1C:
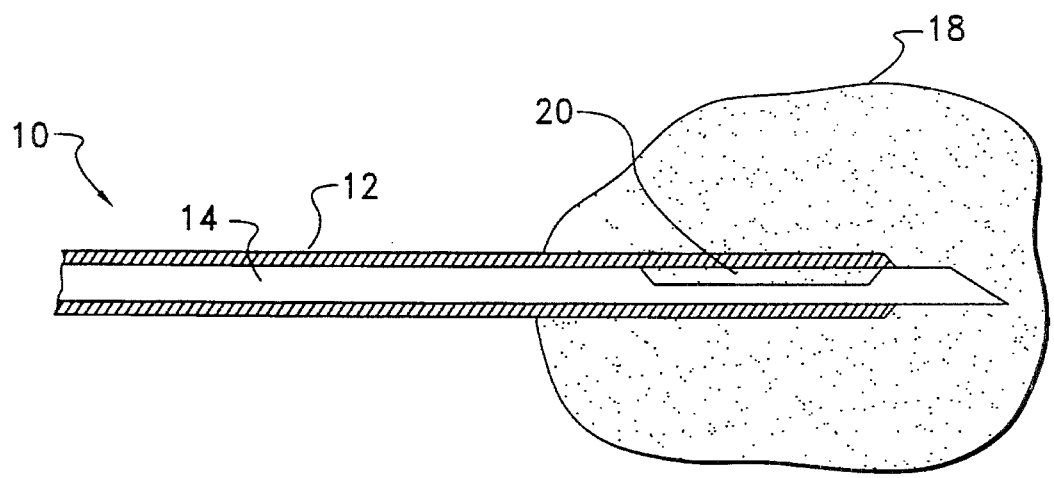

In operation the upper housing 30 is mounted to the lower housing 44 such that the slide members 40 and 42 are suspended immediately above the carriage 60. The user grasps the base 46 using finger grips 48 and 50, while pulling the handle 66 backwards, thereby sliding the carriage 60 to the left until the detent 78 engages the recess 75 on the bottom of carriage 60. In this position, the cannula 12 has been retracted, exposing the specimen notch 16, and the device is half-cocked. Pulling the handle 66 further slides the carriage 60 further to the left until the detent 78 engages the recess 76. In this position, the device is fully cocked. This action compresses the helical drive spring 88 thereby storing energy to propel the carriage 60 to the right once the engagement of the detent 78 is removed. The handle 66 includes a detent release mechanism 94 which engages the detent 78 when the handle 66 is pushed to the right. Engagement of the detent release mechanism 94 with the detent 78 depresses the detent 78, thereby disengaging it from the recess portion 76, and allowing the compressed helical drive spring 88 to propel the carriage 60 to the right. The carriage 60 must follow the path of the cam guide grooves 56 and 58 because of the engagement of the cam follower pin 62 therebetween. The motion followed by carriage 60 during its longitudinal translation is therefore determined by the shape of the cam guide grooves 56 and 58. The shape of the cam guide grooves 56 and 58 is designed such that during the course of the translation of carriage 60, the slide engagement member 64 will selectively and sequentially engage and disengage the slide members 40 and 42 during longitudinal translation. In this way, the cannula 12 and stylet 14 can be made to exhibit the relative motions as illustrated in FIGS. 1A–C.

Figure 7A:
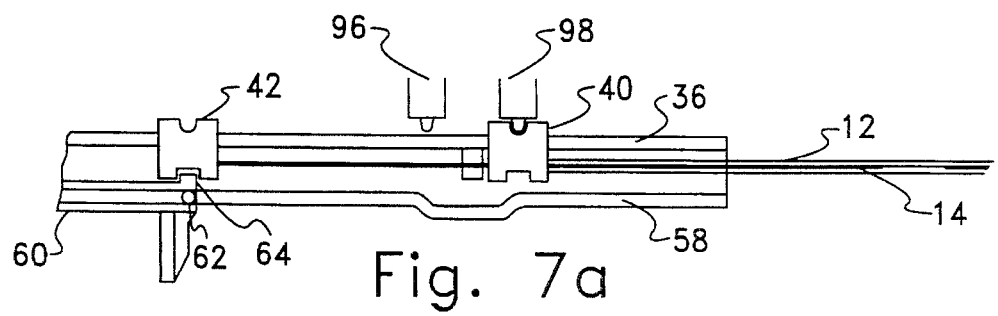
FIGS. 7A–D schematically illustrate sequential steps in the operation of the first embodiment of the present invention.

Referring now to FIG. 7A, the biopsy needle device of the present invention is shown in a schematic cross-sectional view in order to illustrate the operation of the device. The carriage 60 has been retracted fully to the left and rests in the cocked position illustrated in FIG. 5. This cocked position is maintained against the force of the compressed helical drive spring 88 by engagement of the detent 78 with the recess 76 of carriage 60. The slide engagement member 64 has positively engaged the stylet slide member 42 such that any longitudinal displacement of the carriage 60 will produce a like displacement of the stylet slide member 42 along rails 34 and 36. When the handle 66 is pushed back into the biopsy needle device, the detent release mechanism 94 releases the detent 78 from the carriage 60, thereby allowing the compressed helical drive spring 88 to propel the carriage 60 to the right. Such motion also forces the stylet slide member 42 (which is positively engaged with the carriage 60) to be displaced on the rails 34 and 36, thereby forcing the stylet 14 out of the cannula 12 and into the tissue to be sampled.

Figure 7B:
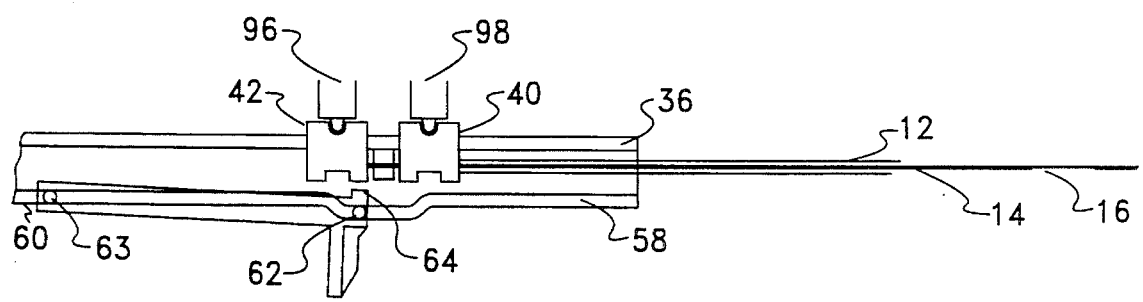

As shown in FIG. 7B, once the stylet 14 has extended a sufficient amount from the cannula 12 (far enough to completely expose the specimen notch 16), the stylet slide member 42 is captured and retained by a spring biased ball bearing detent 96. At this point, the cam guide grooves 56 and 58 turn downward, forcing the cam follower pin 62, the carriage 60 and the slide engagement member 64 to follow a similar downward motion. Such downward motion causes a disengagement of the slide member 42 from the slide engagement member 64. The stylet slide member 42 is thereafter retained in this position by the stylet slide detent 96.

Figure 7C:
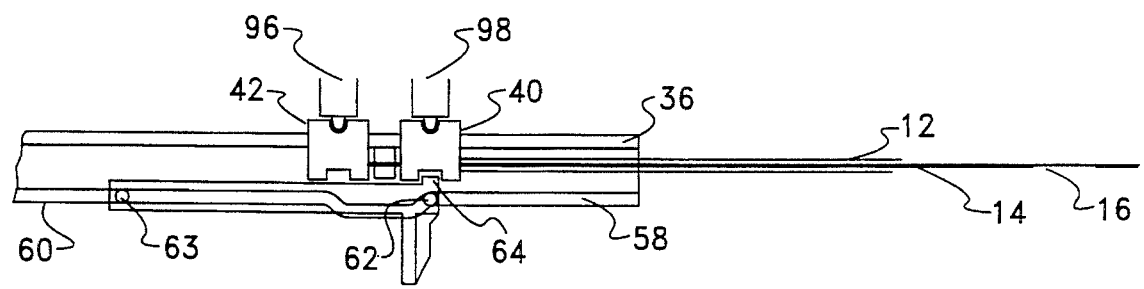
Figure 7D:
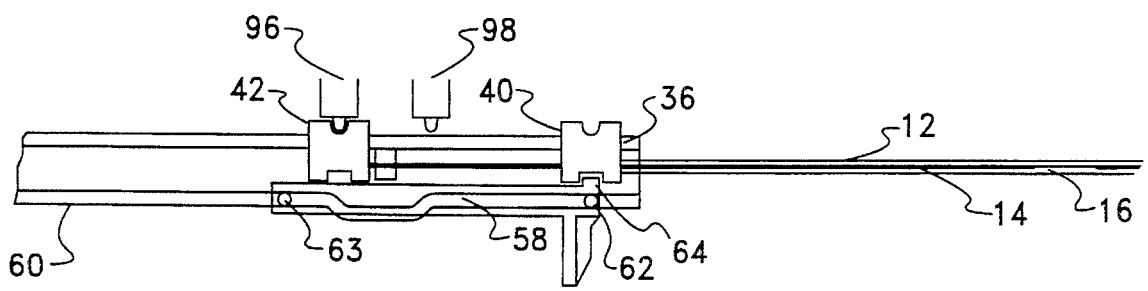

The carriage 60 continues its translation to the right, however the cam guide groove has placed the carriage 60 at a level which is too low to engage either of the slides 40 and 42. As shown in FIG. 7C, the cam guide groove eventually turns upward toward its original elevation, bringing the cam follower pin 62, carriage 60 and slide engagement member 64 into a position to positively engage the cannula slide member 40. Up to this point, the cannula slide member 40 has been retained in this position by the cannula slide detent 98. Once the carriage 60 has engaged the cannula slide member 40, the force of the helical drive spring 88 causes the cannula drive member 40 to disengage from the cannula slide detent 98, thereby longitudinally displacing the cannula 12 to the right. This displacement causes the cannula 12 to cut off the tissue specimen retained in the specimen notch 16 of the stylet 14, thereby completing the biopsy tissue sampling. As shown in FIG. 7D, the sampled tissue is now retained completely within the cannula 12 and the biopsy needle device may be withdrawn from the patient for subsequent removal of the tissue sample.

The configuration of the device as illustrated in FIG. 7D is the uncocked position in which the helical drive spring 88 is not compressed. When the biopsy needle device is to be cocked in preparation for a biopsy procedure, the handle 66 is withdrawn from the device thereby moving the carriage 60 to the left. The carriage 60 will follow the relative path of the cam guide grooves 56 and 58 because of its coupling with the cam follower pin 62. Such motion causes the cannula slide member 40 to translate to the left until it is engaged with the cannula slide detent 98. At this point, the carriage 60 moves in a downward direction following the cam guide grooves 56 and 58. This downward displacement causes the slide engagement member 64 to release the cannula slide 40 while the carriage 60 continues its leftward displacement. The cam guide grooves 56 and 58 will eventually cause the carriage 60 to move in an upward direction, thereby engaging the stylet slide member 42 (which was held in position by stylet slide detent 96) and causing it to displace to the left with the carriage 60. When fully cocked, the detent 78 is engaged with the recess space 76, and the carriage 60 and slide members 40 and 42 are in the relative positions illustrated in FIG. 7A. Insertion of the handle 66 into the biopsy needle device will then begin the automatic biopsy sampling as described in the steps illustrated in FIGS. 7A–D.

Figure 8A:
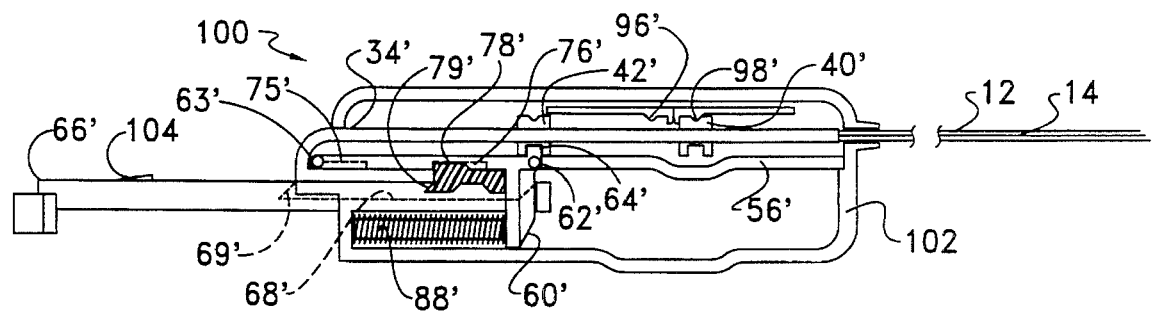
FIGS. 8A–C schematically illustrate sequential steps in the operation of a second embodiment of the present invention.
Figure 8B:
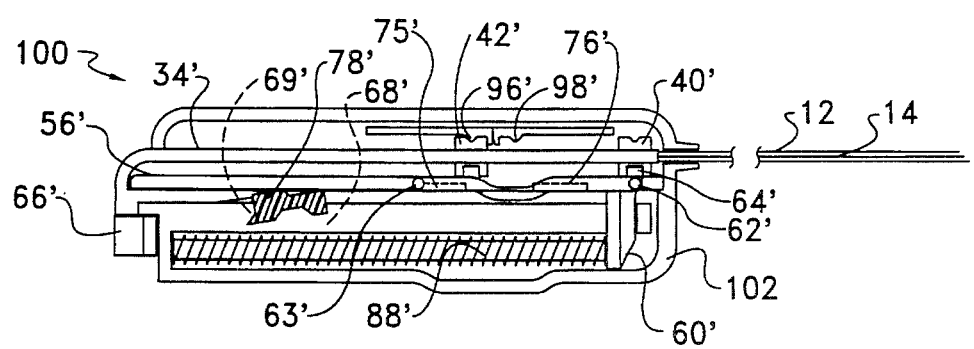

Referring now to FIG. 8, there is illustrated a second embodiment of the present invention, indicated generally at 100. The second embodiment of FIG. 8 is similar to the first embodiment of FIG. 7, the major differences being that the rails 34' upon which the slide members 40' and 42' slide, project from the sides of the housing 102 rather than from the top, and the carriage 60' is engaged with the handle 66' below the carriage 60' rather than above it. The operation of the biopsy needle device 100 follows the same sequence of events illustrated schematically in FIG. 7. Referring to FIG. 8A, when the handle 66' is fully retracted, the detent 78' engages with the recess 76', thereby retaining the helical drive spring 88' in a compressed state. In this position the cannula slide member 40' and the stylet slide member 42' are fully retracted, causing the sharp end of the stylet 14 to slightly protrude from the end of the cannula 12. The handle 66' is equipped with a safety 104 which engages the housing 102 to prevent accidental energization of the biopsy needle device. It is necessary to depress safety 104 to permit movement of the handle 66' into the housing to activate the device.

Figure 8C:
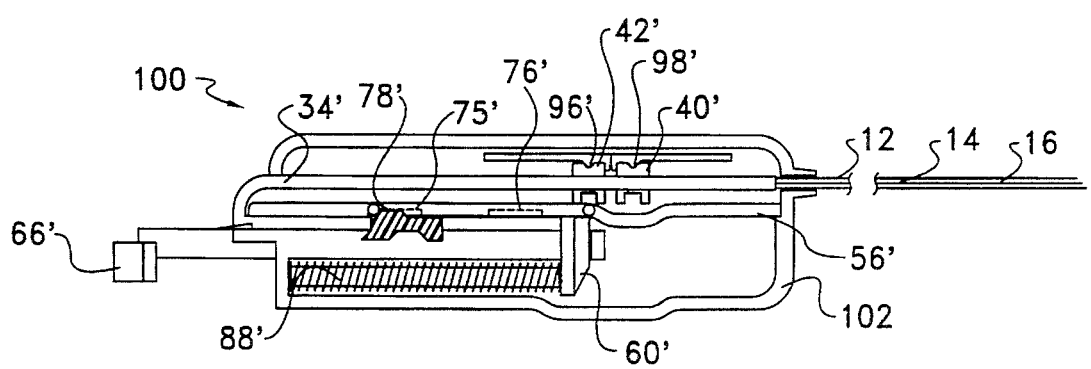
Figure 9:
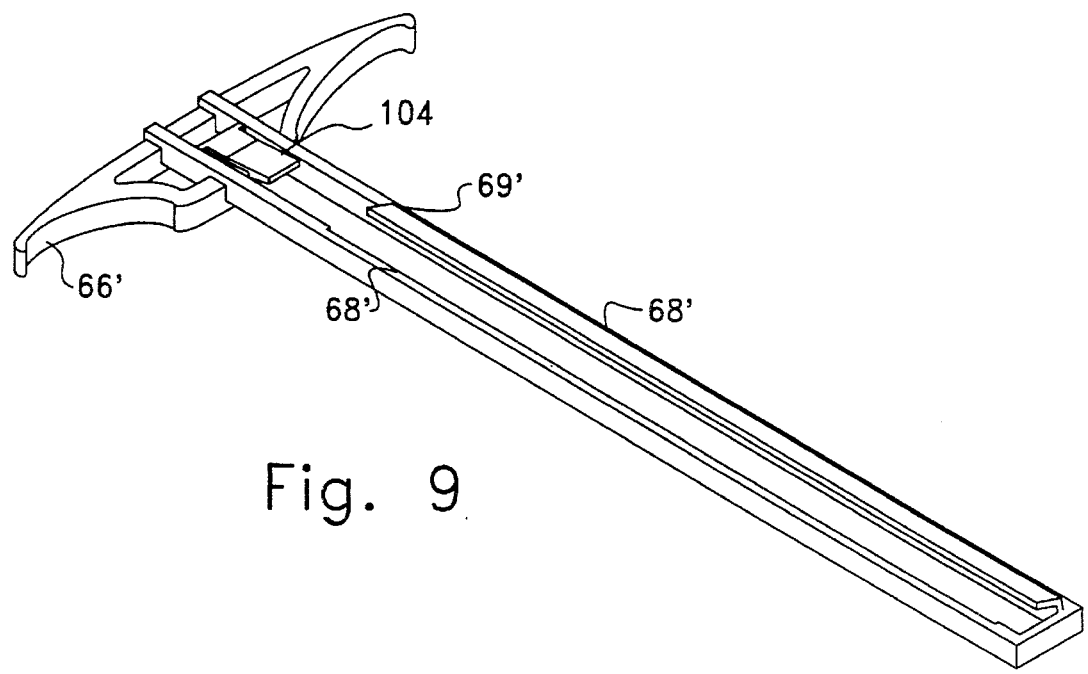
FIG. 9 is a perspective view of a handle of the second embodiment of the present invention.

As shown in FIGS. 8A and 9, the handle 66' includes opposing channels 68' terminating in an angled offset 69'. The detent 78' normally rides within the channels 68'. When the safety 104 is released, the handle 66' can be is inserted back into the housing 102, until the angled offest 69' engages the beveled tip 79' of the detent 78', thereby depressing the detent 78' and disengaging it from the recess 76'. There is then nothing to prevent the helical drive spring 88' from acting upon the carriage 60' and driving the carriage to the right. In analogous fashion to the sequence of events illustrated in FIG. 7, the carriage 60 propels the stylet slide member 42' to the right until it engages the stylet detent 96', the carriage 60' disengages from the stylet slide member 42' and positively engages the cannula slide member 40', and the carriage 60 propels the cannula slide member 40' to the right until it reaches the end of cam guide groove 56'. As shown in FIG. 8C, in order to retrieve the captured tissue from specimen notch 16, the handle 66' is retracted until the detent 78' engages the recess 75'. In this position, the device is held in place with the cannula 12 retracted from the stylet 14, thereby exposing the specimen notch 16.

Figure 10:
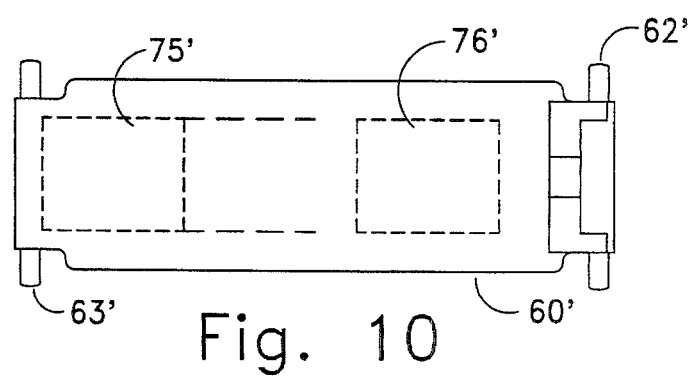
FIG. 10 is a plan view of a carriage of the second embodiment of the present invention.
Figure 11:
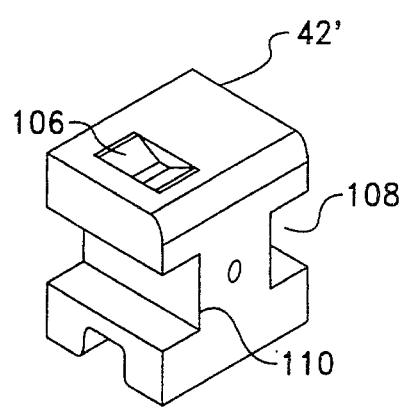
FIG. 11 is a perspective view of a stylet slide member of the second embodiment of the present invention.

A top plan view of the carriage 60' is illustrated In FIG. 10. Visible in this view are the cam follower pins 62' and 63', as well as the recesses 75' and 76'. The stylet slide member 42' is illustrated in FIG. 11, with the stylet 14 removed therefrom for clarity of illustration. The slide member 42' includes channels 108 and 110 which engage rails 34' and 36' and slide thereupon. The top of slide member 42' includes a recess 106 for engagement with the slide detent 96'. It will be appreciated by those skilled in the art that the cannula slide member 40' is substantially identical to the stylet slide member 42'.

It will be further appreciated by those skilled in the art that the biopsy needle device of the present invention exhibits several advantages over prior art needle biopsy devices. The simplicity of design of the present invention offers significant advantages in ease of assembly, cost of materials and reliability of operation. It is therefore possible to offer the user a simpler, less expensive and more reliable device. The use of a single driving carriage to selectively engage and disengage the stylet and cannula result in fewer moving parts and a less complicated design. An additional advantage is obtained by the positive engagement of the slide engagement member 64 with the slide members 40 and 42, physically interlocking the devices during their joint displacement. Furthermore, the small number of parts required for the present invention result in a compact profile and a light weight device, both of which are of paramount importance when utilizing the device in an actual biopsy procedure.

While the invention has been described in detail in the foregoing description, the same is to be considered as illustrative and not restrictive in character, it being understood that only the preferred embodiments have been shown and described, and that all changes and modifications that come within the spirit of the invention are desired to be protected.

What is claimed:

1. A biopsy needle device, comprising:
   a housing;
   a cannula;
   a stylet;
   a cannula slide member coupled to the cannula and operative to slide on the housing along a longitudinal axis in a first direction;
   a stylet slide member coupled to the stylet and operative to slide on the housing along the longitudinal axis in the first direction such that the stylet is carried partially within the cannula;
   a carriage slidably disposed within the housing and having a slide engagement member operative to sequentially engage the stylet slide member and the cannula slide member;
   drive means for propelling the carriage in the first direction within the housing;
   a cam guide pin coupled to the carriage; and
   a cam guide groove configured to slidably receive the cam guide pin therein and operative to reciprocate the carriage in a second direction substantially perpendicular to the first direction while the carriage is translating in the first direction;
   wherein when the drive means propels the carriage, the carriage engages the stylet slide member to translate stylet slide member in the first direction, disengages the stylet slide member by moving in said second direction, and reciprocates in said second direction to engage the cannula slide member as the guide pin slides along the groove, and translates the cannula slide member in the first direction.

2. The biopsy needle device of claim 1, further comprising:
   rail means defined in the housing parallel to the longitudinal axis; and
   means on the stylet and cannula slide members to slidingly engage the rail means.

3. The biopsy needle device of claim 1, wherein the drive means comprises a helical spring.

4. The biopsy needle device of claim 3, further comprising:
   a recess defined in a surface of the carriage; and
   a detent defined in the housing operative to releasably engage the recess when the helical spring is compressed.

5. The biopsy needle of claim 4, further comprising:
   a detent release mechanism operative to disengage the detent from the recess void, thereby releasing the compressed spring to translate the carriage in the first direction.

6. The biopsy needle device of claim 1, further comprising:
   a stylet detent for engaging and holding the stylet slide member when the carriage disengages the stylet slide member; and
   a cannula detent for engaging and holding the cannula slide member until the carriage engages the cannula slide member.

7. The biopsy needle device of claim 6, wherein the stylet detent and the cannula detent comprise ball bearings biased toward the stylet slide member and the cannula slide member, respectively.

8. The biopsy needle device of claim 1, wherein the slide engagement member comprises a raised post sized to engage a first recess on a first bottom side of the cannula slide member and a second recess on a second bottom side of the stylet slide member.

9. A biopsy needle device comprising:
   a cannula;
   a cannula slide member coupled to the cannula and operative to slide in a first direction;
   a stylet;
   a stylet slide member coupled to the stylet and operative to slide in the first direction such that the stylet is carried partially within the cannula; and
   a carriage;
   means for reciprocating the carriage in a second direction while translating the carriage in the first direction, the second direction being substantially perpendicular to the first direction;
   wherein the carriage engages the stylet slide member, translates the stylet slide member in the first direction, disengages the stylet slide member by moving in said second direction, and reciprocates in said second direction to engage the cannula slide member and translate the cannula slide member in the first direction.

10. The biopsy needle device of claim 9, wherein the carriage includes a slide engagement member operative to sequentially engage the stylet slide member and the cannula slide member.

11. The biopsy needle device of claim 9, further comprising:
    a cam guide pin coupled to the carriage; and
    a cam guide groove, wherein the reciprocating is produced by the cam guide pin following the cam guide groove during translation in the first direction.

12. The biopsy needle device of claim 9, further comprising:

drive means coupled to the carriage for translating the carriage in the first direction.

13. The biopsy needle device of claim 12, wherein the drive means comprises a helical spring.

14. A method for performing a tissue biopsy, comprising the steps of:

(a) engaging a carriage with a stylet;

(b) translating the carriage and the stylet in a first direction;

(c) reciprocating the carriage in a second direction while translating the carriage in the first direction, the second direction being substantially perpendicular to the first direction;

(d) disengaging the carriage from the stylet during the reciprocation in the second direction of step (c);

(e) engaging the carriage with a cannula during the reciprocation in the second direction of step (c); and (f) translating the carriage and the cannula in the first direction.

15. The method of claim 14, wherein step (b) includes:

(b.1) displacing the carriage in a third direction, the third direction being substantially opposite the first direction;

(b.2) compressing a biasing means concomitant with the displacement of the carriage; and (b.3) allowing the biasing means to expand and act upon the carriage, causing translation of the carriage in the first direction.

16. The method of claim 14, wherein step (c) comprises:

(c.1) providing a cam guide pin coupled to the carriage; and (c.2) securing the cam guide pin within a cam guide groove, wherein the cam guide groove transitions from a first axis to a second axis and back to the first axis along the length of the cam guide groove, the first and second axes being substantially parallel.

17. The method of claim 14, comprising the further step of:

(g) engaging and holding the stylet with a detent concomitant with disengaging the carriage from the stylet.

18. The method of claim 14, comprising the further step of:

(g) engaging and holding the cannula with a detent prior to engaging the carriage with the cannula.

19. The method of claim 14, further comprising the step of:

(g) retaining the stylet and the cannula on at least one rail extending in the first direction.

* * * * *